United States Patent [19]

Pincus et al.

[11] Patent Number: 5,191,524

[45] Date of Patent: Mar. 2, 1993

[54] APPROXIMATE ENTROPY

[76] Inventors: Steven M. Pincus, 990 Moose Hill Rd., Guilford, Conn. 06437; Robert A. Neidorff, 39 Stowell Rd., Bedford, N.H. 03102

[21] Appl. No.: 404,737

[22] Filed: Sep. 8, 1989

[51] Int. Cl.$^5$ ............................................. G06F 15/42
[52] U.S. Cl. ................................................ 364/413.05
[58] Field of Search ...................... 364/413.02, 413.05, 364/413.06, 413.03; 128/703, 706

[56] References Cited

U.S. PATENT DOCUMENTS

| | | | |
|---|---|---|---|
| 4,018,219 | 4/1977 | Hojaiban ...................... | 364/413.03 |
| 4,680,708 | 7/1987 | Ambos et al. .................. | 128/703 X |
| 4,732,157 | 3/1988 | Kaplan et al. .................. | 128/696 |
| 4,802,491 | 2/1989 | Cohen et al. .................... | 128/702 |
| 4,934,374 | 6/1990 | Ostlund et al. .................. | 128/695 |
| 4,974,162 | 11/1990 | Siegel et al. .................... | 364/413.06 |

OTHER PUBLICATIONS

*Crit. Care Med.*, Zbilut et al., "Decreased Heart Rate Variability in Significant Cardiac Events", vol. 16, No. 1, 1988, pp. 64–66 (abstract only).

*Electroencephalogr. Clin. Neurophysiol.*, Inouye et al., "Quantification of EEG irregularity . . . ", vol. 79, No. 3, 1991, pp. 204–210, (abstract only).

Gleick, J., *Chaos: Making a New Science*, Viking Penguin Inc., New York, N.Y. (9187), 275–300.

Eckmann, J. P., and Ruelle, D., "Ergodic Theory of Chaos and Strange Attractors", *Reviews of Modern Physics*, 57(3), Jul. 1985.

Browne, M., "In Heartbeat, Predictability is Worse than Chaos", *New York Times*, Jan. 17, 1989.

*Primary Examiner*—Roy N. Envall, Jr.
*Assistant Examiner*—David Huntley
*Attorney, Agent, or Firm*—Hamilton, Brook, Smith & Reynolds

[57] ABSTRACT

An approximation of entropy is determined on a set of data by comparing subsets of the data. The comparison reveals the regularity and stability of similar patterns amongst subsets of the data. The comparisons perform such that the contribution of noise to measurement of the regularity and stability is minimized. Quantitative values are assigned to measure the degree of regularity and stability. From these quantitative values a single output measure is generated indicative of the amount of patternness of the sequence of data. The calculations required to determine this approximate entropy are preferably performed within a data processing system. Numerous peripheral devices may be attached to such a data processing system. The types of data for which the approximate entropy may be calculated include any sets of data wherein the amount of patternness is sought.

22 Claims, 4 Drawing Sheets

| SLOT | U(1) | U(2) | U(3) | U(4) | U(5) | U(6) | U(7) | U(8) | U(9) |
|---|---|---|---|---|---|---|---|---|---|
| VALUE | 1 | 0 | 1 | 0 | 1 | 0 | 1 | 0 | 1 |
*Fig. 4A*
| SLOT | U(1) | U(2) | U(3) | U(4) | U(5) | U(6) | U(7) | U(8) | U(9) |
|---|---|---|---|---|---|---|---|---|---|
| VALUE | * | * | 1 | * | * | 0 | * | * | 1 |
\* Random where both zero and one occur with probability ½
*Fig. 4B*
AN IMPERFECT WORLD
IDEAL CURVE (SINE WAVE)
*Fig. 6A*
EFFECTS OF STEADY, SMALL NOISE
   NEGLIGIBLE ON MEAN, S.D.
   DOMINANT ON ENTROPY
*Fig. 6B*
EFFECT OF INFREQUENT LARGE ERRORS
   SIGNIFICANT ON MEAN, S.D.
   NEGLIGIBLE ON ENTROPY
   ROBUSTNESS OF ApEn TO ARTIFACTS
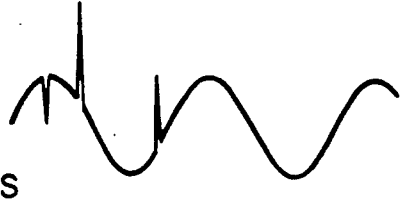
*Fig. 6C*

APPROXIMATE ENTROPY

BACKGROUND OF THE INVENTION

Diagnosis of many medical conditions requires the collection and analysis of medical data. In interpreting this data doctors and other medical personnel have generally applied a number of rules of thumb, or qualitative assessments, to reach their diagnosis. These rules of thumb have proven to be quite useful but are not comprehensive, for certain ailments and abnormalities cannot be adequately identified merely by applying currently established rules of thumb. One example where rules of thumb are applied is in monitoring electrocardiograph (EKG) data. EKG data is typically presented as a graphical output of a patient's heart activity. Doctors look for recognizable abnormalities and particular flags in the EKG data, as warning signals of health problems. They can discern certain abnormalities amongst this data by visually inspecting the graphical output; however, other important, more subtle abnormalities may go undetected. As such, the visual examination of data does not provide a complete diagnostic tool because some potentially significant abnormalities in the data are not v apparent from visual inspection.

SUMMARY OF THE INVENTION

The present invention concerns the determination of the amount of patternness of a set of data. This data may be medical data or any other data for which it would be useful to know the amount of patternness present in the data. In determining the amount of patternness, subsets of data are first compared to determine the regularity and stability of similar patterns among the subsets. The detrimental effects of noise in these comparisons are minimized by the imposition of an imbedded algorithm. Intermediate values are then assigned to quantify the regularity and stability of similar patterns among the subsets that are compared. The output measure of patternness is based on the average of these assigned intermediate values. This measure is forwarded as an output signal to its destination.

In the preferred embodiment, the set of data is medical data, and the measure of patternness is an approximation of entropy. Moreover, the contribution of noise to this measure is minimized as noted above, with the sub-algorithm which comprises a specified filter.

A particular application for which the approximation of entropy may be valuable is in the analysis of electrocardiograph data such as beat-to-beat heart rate data derived from an EKG. When used in such an application, the R-R intervals between consecutive beats are first extracted from EKG data. These R-R intervals are a standard measure of the length of heartbeats. They are then averaged for a given length of time (preferably specified by the user) to produce a set of R-R interval averages. These averages are then analyzed as described above.

Another application for which the application of entropy may be valuable is in the analysis of hormone secretion behavior, measured typically from blood samples. Pulsatile secretions are found in many hormones, so there is great potential for this measure to identify deviations from normal secretion patterns, and to identify diseases pre-onset of symptoms. The data for the measure of patternness in this case is a series of blood level measurements of a specified hormone.

The present invention may also be used with other types of medical data. For instance, it may be used with electroencephalograph data, electro-ocolgram data, electromyogram data, and respiratory measurement data. To analyze data via the present invention, it is often necessary to first convert the data into digital form before processing it.

The present invention may also have significant non-medical applications. It may be used to analyze stock market data, such as the Dow Jones index, individual stock prices, and bond prices over time. It may also be used to analyze aerodynamic, hydrodynamic, and astronautic data, such as velocities, momenta, pressure, position data, etc. and especially to provide a figure-of-merit for turbulent behavior of these data.

The processing of the data is carried out by a data processing system. The data processing system should include a comparison means for performing the above described comparing step and a filtering means for minimizing the effects of noise in the data on the computation. Both of these means may be incorporated within a single processor. Such a processor generates a single number as an approximation of entropy. The approximation of entropy may be forwarded to a number of different output peripheral devices. For instance, it may be output to an alarm that signals when the approximate entropy lies outside a safe range. In addition, it may be employed with a meter that displays the approximate entropy, as well as with an automated dispensing means that automatically dispenses medication in response to the approximate entropy. Further, a storage device may be attached to the data processing system to record the approximate entropy over a period of time.

BRIEF DESCRIPTION OF THE DRAWINGS

FIGS. 4a and 4b show sample sets of data.

FIGS. 6a, 6b and 6c show three different sample sets of data.

DETAILED DESCRIPTION OF THE PREFERRED EMBODIMENT

The preferred embodiment of the present invention concerns the determination of the amount of patternness in sets of data, especially sets of medical data. In particular, a data processing system 2 is utilized to produce a single number measuring the amount of patternness in a set of electrocardiograph (EKG) data. This single number constitutes an approximation of entropy in heart rate data derived from the set of EKG data, and will be referred to hereinafter as approximate entropy. It is useful in determining, from the set of EKG data, both the well-being of the heart and the general well-being of the individual. It is also useful in other applications that will be discussed below.

Figure 1:
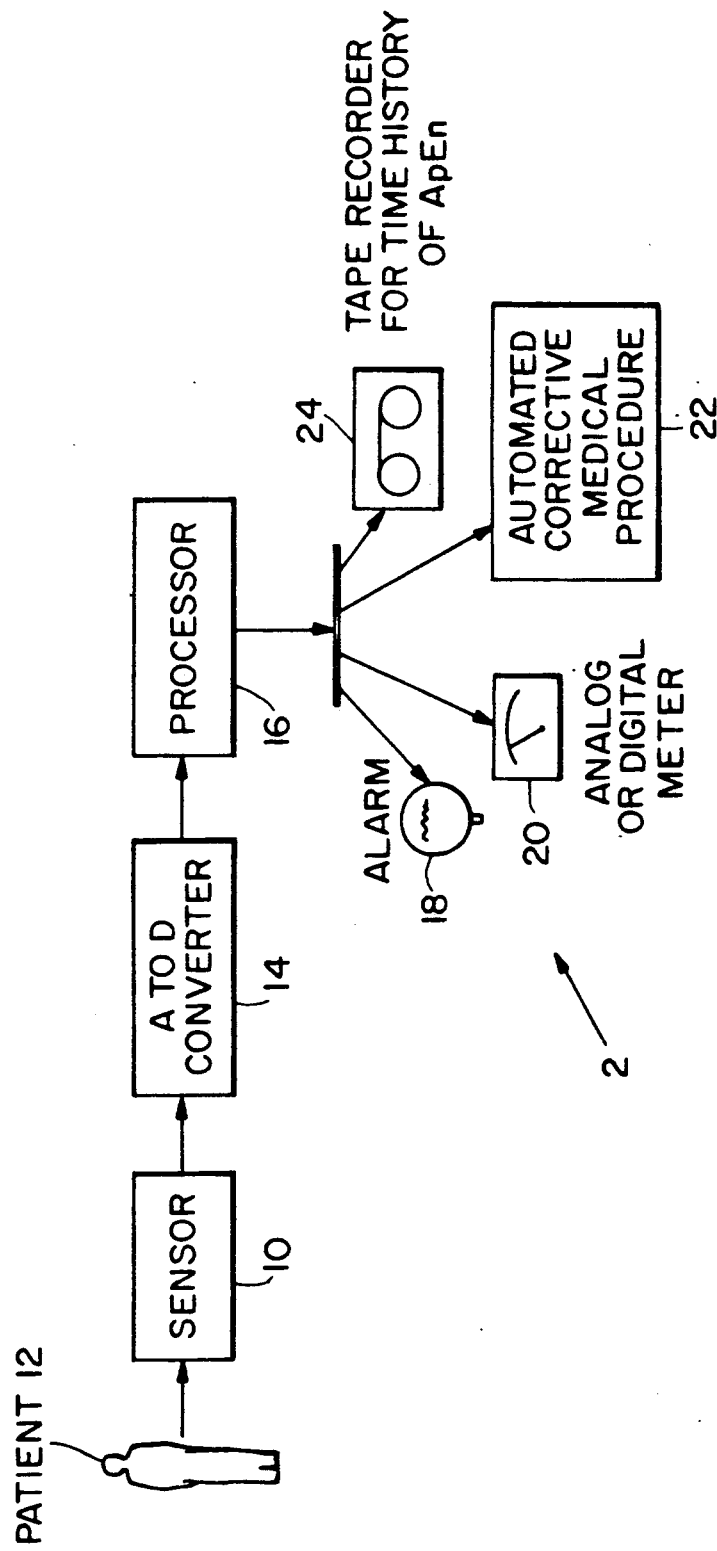
FIG. 1 shows the data processing system that calculates approximate entropy and acts on the calculated value.
Figure 2:
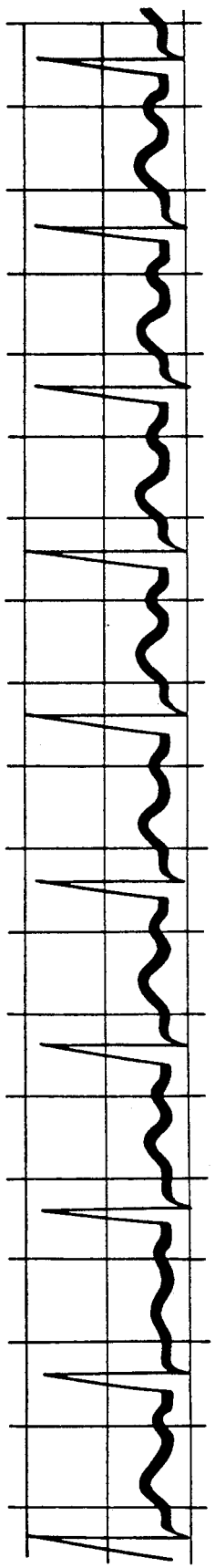
FIG. 2 shows a sample EKG tracing.

FIG. 1 shows the major components of the data processing system used to obtain this approximation of entropy. Specifically, a sensor 10 is applied to a patient 12 to obtain EKG data. Techniques for applying such a sensor 10 are well known in the prior art. Once the sensor 10 is appropriately attached to the patient 12, the sensor begins receiving electromagnetic data relating to the patients heartbeat. This data is typically received in analog form and output as a graph known as a tracing. FIG. 2 shows a typical EKG tracing for a healthy heart.

Figure 3:
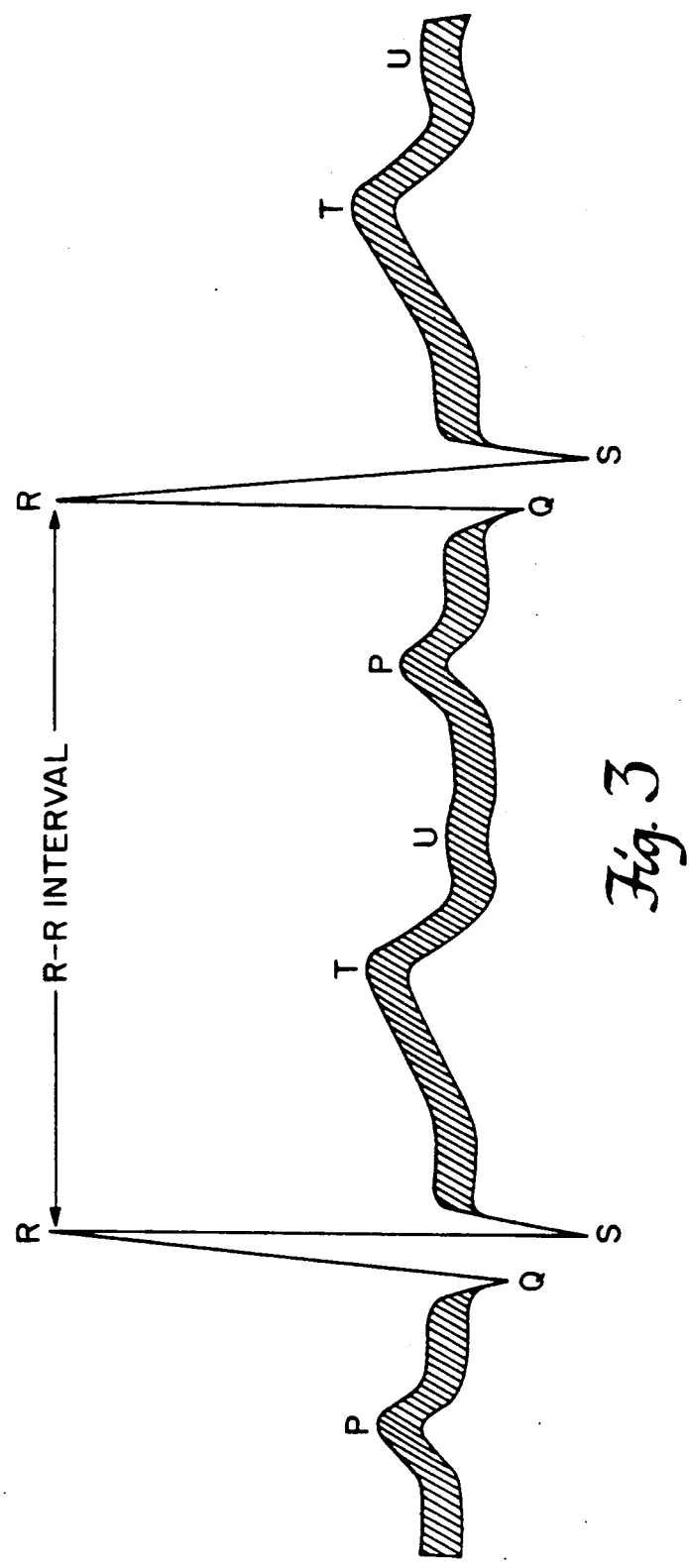
FIG. 3 shows two sample pulses of a heartbeat.

Although the analog EKG data is useful as a graphical representation of the data, it is difficult to process. Hence, the present system includes an analog to digital converter 14 that samples the analog waveform of the EKG tracing to produce a digital representation of the samples. This digital representation is then forwarded to a processing means 16 wherein the digital data is processed to produce the approximate entropy measure. In particular, the data processing system looks at the interbeat intervals in the EKG tracings. The interbeat intervals are measured between the R-portions of consecutive pulses. Two consecutive pulses, and the R-R interval for them, are shown in FIG. 3.

The system extracts the R-R intervals from the EKG data and averages them for a given, user-specified short length of time to produce an average set of R-R intervals. This average set of R-R intervals is processed to obtain the approximate entropy measure. The user can choose to work with the R-R intervals directly too. The processing means 16 contains the appropriate software to perform the necessary calculations to obtain the approximate entropy measure. This software can be written in any of a variety of high level languages such as Fortran, C, Pascal, etc. The details of the software will be discussed more below.

The resulting approximate entropy measure as computed by the processing means 16 can be output to a number of different types of peripheral devices. For instance, the approximate entropy measure can be forwarded to an alarm 18 which indicates when the measure lies outside an acceptable range. Further, the approximate entropy measure can be forwarded to an analog or digital meter 20 that shows the current value of the measure as computed by the processing means. Still further, the approximate entropy measure can be sent to an automated corrective medical procedure device 22. Such a device 22 automatically reacts to remedy a difficulty noted by an unsatisfactory approximate entropy measure. For example, if the approximate entropy measure indicates a low level of a vital hormone, the automated corrective procedure device 22 can excrete a given quantity of the hormone in response to the low approximate entropy measure.

Another alternative is for the approximate entropy measure to be recorded on a tape recording or other recording means 24 such that a time history of the approximate entropy measure is kept. Each of these peripherals 18, 20, 20, 22 and 24 need not exist in isolation. The system can be configured such that all of these devices are connected simultaneously to the processing means 16. Moreover, peripheral devices other than those described can be attached to the processing system. These suggested devices are not meant to be exhaustive of the personal devices that lie within the scope of the present invention.

Such a measure of patternness of a set of time related data is especially useful in medical applications. Medical personnel have for years visually examined hard copies of medical data presented in graphical form to attempt to discern abnormalities in the data. Such efforts, however, can only discern patternness at a superficial level that lacks the usefulness and completeness of the measure of the present invention. Moreover, past efforts have not been able to distill the patternness into a single comprehensive measure that is both readily usable and robust to noise.

The present invention can be used with medical data such as electrocardiograph (EKG) data, electroencephalogram (EEG) data, electro oculogram (EOG) data, electromyogram (EMG) data, and respiratory data such as ventilation pulses that measure tidal volume. It can also be used to analyze the patternness and pulse stability exhibited in hormone secretion. Further, it can be used to analyze non-medical data, such as stock market data over time; and aerodynamic, hydrodynamic, and astronautic data, to provide a figure-of-merit for turbulent behavior of these data. This list is not intended to be exhaustive of the potential applications of the present invention; rather it is merely intended to be illustrative. The present invention can, in fact, be useful anytime wherein knowing the degree of patternness in a set of data is useful.

Approximate entropy, applied to heartbeat data, can potentially be used as a general barometer of human health. It has already been found to distinguish sick neonates from healthy neonates in a study conducted by one of the inventors at the Yale University School of Medicine. In this study, performed with two faculty pediatricians, data were taken for 15 healthy neonates and 9 asphyxiated neonates. Their heart rates were averaged every 5 seconds, for 1000 measurements. The approximate entropy was lower for the sick group, as anticipated, corresponding to greater patternness. The sick group had an approximate entropy average of $0.80 \pm 0.31$ versus $1.22 \pm 0.12$ (mean$\pm 1$ S.D.) for healthy neonates. The significance of this result was $p = 0.003$ (t-test). Comparisons between the two groups, using the clinically used measure of heartbeat variability, VAR (standard deviation) did not show a significant difference between the two groups ($p = 0.14$). Tables 1a and 1b show the data from this study for both the healthy and sick groups, respectively. Moreover, a serial study on a septic infant with persistent pulmonary hypertension showed a large steady increase in approximate entropy with recovery, further confirming approximate entropy as a barometer of general health. Additionally, approximate entropy discerned the poor health of several of the infants who were otherwise without recognizable EKG abnormalities.

TABLE 1a

| HEALTH | ApEn | VAR | WT (GMS.) | AGE (WKS.) | SEX |
|---|---|---|---|---|---|
| 1. HEALTHY | 0.94 | 5.57 | 2050 | 36 | M |
| 2. HEALTHY | 1.08 | 6.99 | 1750 | 33 | F |
| 3. HEALTHY | 1.11 | 6.65 | 2010 | 31 | M |
| 4. HEALTHY | 1.12 | 10.29 | 1890 | 33 | F |
| 5. HEALTHY | 1.16 | 8.13 | 1800 | 34 | F |
| 6. HEALTHY | 1.20 | 9.42 | 550 | 24 | F |
| 7. HEALTHY | 1.24 | 8.53 | 1820 | 37 | F |
| 8. HEALTHY | 1.25 | 17.65 | 2020 | 41 | M |
| 9. HEALTHY | 1.27 | 8.56 | 3650 | 40 | M |
| 10. HEALTHY | 1.27 | 11.08 | 1300 | 34 | F |
| 11. HEALTHY | 1.29 | 11.95 | 1600 | 36 | F |
| 12. HEALTHY | 1.30 | 10.31 | 1730 | 33 | F |
| 13. HEALTHY | 1.30 | 9.54 | 3490 | 40 | F |
| 14. HEALTHY | 1.38 | 14.31 | 3100 | 40 | M |
| 15. HEALTHY | 1.40 | 15.10 | 4360 | 42 | M |
| SUMMARY STATISTICS: (MEAN +/- SD) | | | | | |
| ApEn: | 1.22 +/- 0.12 | | | | |
| VAR: | 10.27 +/- 3.33 | | | | |
| WT: | 2210 +/- 1000 | | | | |
| AGE: | 35.6 +/- 4.7 | | | | |

TABLE 1b

| HEALTH | ApEn | VAR | WT (GMS.) | AGE (WKS.) | SEX |
| --- | --- | --- | --- | --- | --- |
| 1. CONG. HF | 0.32 | 4.34 | 2430 | 34 | M |
| 2. PPH | 0.46 | 6.56 | 1090 | 27 | M |
| 3. PPH | 0.59 | 7.37 | 1090 | 27 | M |
| 4. CONG. HF | 0.69 | 10.49 | 3810 | 37 | F |
| 5. SEVERE RDS | 0.73 | 8.13 | 870 | 26 | M |
| 6. PPH | 1.02 | 11.70 | 1090 | 27 | M |
| 7. CONF, HF, DIAPH. HERN. | 1.03 | 7.88 | 2670 | 39 | M |
| 8. CONG. HF (TRI18) | 1.15 | 11.61 | 2270 | 39 | F |
| 9. GI OBST., TEF/Asp | 1.19 | 8.24 | 2640 | 40 | F |

CONG. HF: CONGENITAL HEART FAILURE
DIAPH. HERN.: DIAPHRAGMATIC HERNIA
GI OBST.: GASTROINTESTINAL OBSTRUCTION
PPH: PERSISTENT PULMONARY HYPERTENSION
RDS: RESPIRATORY DISTRESS SYNDROME
TEF/Asp: TRACHEO-ESOPHAGEAL FISTULA WITH ASPIRATION
TRI. 18: TRISOMY 18

SUMMARY STATISTICS: (MEAN +/− SD)

| | |
| --- | --- |
| ApEn: | 0.80 +/− 0.31 |
| VAR: | 8.48 +/− 2.42 |
| WT: | 2000 +/− 1010 |
| AGE: | 32.9 +/− 6.1 |

Moreover, it may be used to monitor fetal heart data so as to indicate fetal distress, and it may be used in monitoring the heart rate of infants to eliminate deaths attributable to sudden infant death syndrome (SIDS). Furthermore, the approximate entropy measure can be used to determine subtle arrhythmias that are that are not otherwise detectable.

Entropy refers to the degree of randomness, or disorder, within a system or set of data. Randomness is perhaps most easily understood as being the opposite of patternness (i.e. not patterned). Thus, the patternness of a particular set of data is inversely related to the randomness of the set of data. From this relationship, it can be seen that as the amount of patternness increases the level of entropy decreases. Thus, by measuring an approximation of entropy on a set of data, the present invention is measuring the degree of patternness within the data.

There are several reasons why the approximate entropy measure may detect a broad range of problems in the human body heretofore undetected. It has recently become known that much of the human body exhibits chaotic behavior when functioning properly. As noted in Gleick, James, Chaos: Making a New Science, 1987, pp. 275-300, where he summarizes numerous primary sources, a change in the nature of this normally chaotic behavior may be a signal that problems exist. Unfortunately, the changes in this chaotic behavior usually are not readily discernible by visual review of the data that measure the body's function (EKG, EEG, etc.). Approximate entropy provides a measure for discerning (subtle) changes in the degree of the chaotic behavior exhibited, and hence in identifying improper body function.

The ability of approximate entropy to directly measure feedback system change in many systems may allow this measure to predict ailments in the human body pre-onset. Many systems of the human body exhibit coupled, or feedback behavior when functioning properly. For example, the male reproductive system can be viewed as a feedback loop. Specifically, the hormone LHRH determines LH production, which determines testosterone production, and the testosterone production, in turn, determines LHRH production. The heart, consisting of the sinoatrial node and the atrioventricular junction, is another example of such a coupled feedback mechanism. Changes in this feedback loop, either in extent or in nature, may cause or indicate disease Changes in feedback are often reflected in corresponding changes in the entropy and approximate entropy of systems. Decoupling and lessening feedback is explicitly noted by decreasing entropy and approximate entropy in the system. This barometric property of entropy may have two important medical implications. First, it may allow for the identification of insidious diseases not otherwise detectable, pre-onset of symptoms, and second, it may help to identify the physiologic system change that is the cause of some diseases.

The approximate entropy measure is an approximation of Kolmogorov-Sinai (K.S) entropy which can be expressed mathematically as:

$$\text{Entropy} = \lim_{r \to 0} \lim_{m \to \infty} \lim_{n \to \infty} [\Phi^m(r) - \Phi^{m+1}(r)]$$

This formula is disclosed in the article "Ergodic Theory of Chaos and Strange Attractors", by J. P. Eckmann and D. Ruelle in Reviews of Modern Physics, vol. 57, no. 3, July 1985, with $\Phi$ as given as in formula 5.8, page 650. Unfortunately, this formula has little general practical utility, for two reasons. First, accurate entropy calculations for most data sets cannot be performed in "finite" time; that is less than multiple of years of computer time per calculation. Part of the difficulty in calculating K-S entropy lies in that it is a triple-limit and that $\Phi$ requires a number of steps to define. Also, the computational time to insure accuracy grows exponentially with m. Second, the formula degrades badly (disintegrates) when noise is present because the presence of noise in the data causes the entropy calculation to explode to very high values. With Kolmogorov-Sinai entropy noise considerations dominate other system characteristics. Therefore, it has proven to be a measure that lacks robustness. Moreover, entropy is not a well-known measure, even among mathematicians. There is generally a lack of any statistics, practical or otherwise, to address patternness. The present invention, in contrast, overcomes these difficulties, and provides an approximation of entropy that is both readily calculated for any time-series data and robust to noise.

The notions of patternness and approximate entropy are perhaps more easily conceived than calculated. It is not obvious how one goes about precisely determining the amount of patternness in a given set of data. K-S entropy is one approach to determine patterness, but it suffers from the difficulties noted above.

The basic approach of the method of the present invention is to compare subsets of the data so as to look for patterns amongst the subsets. All groups of contiguous subsets of the data are compared against each other, in search of the proportion of similar patterns for each "template" pattern. The approximate entropy measure is derived from an average of these proportions.

A step-by-step computation of approximate entropy will next be explained for the preferred embodiment. The computation is performed for the example series of data given in FIG. 4a, a "perfectly patterned" series of alternating 0's and 1's. A more mathematically formal description of the preferred embodiment follows.

FIG. 4a shows an example series of data that is useful in explaining the mechanics of calculating the approximate entropy measure. In this preferred embodiment, the processing means 16 receives such a series of data and begins processing it. Two system parameters are set before the processing means 16 calculates the approximate entropy measure. These parameters can be either encoded in the software or requested from the user of the system. These parameters include a value r, which stands for radius, and is a filter factor, and a value m which is the length of a run or template pattern length. Defining these variables as fixed is quite different from what is done with K-S entropy, for K-S entropy is calculated as a limiting value as these variables approach zero and infinity, respectively. Moreover, the number of elements in the set of data is fixed in the present invention. K-S entropy, on the other hand, requires that the number of elements approaches infinity. The significance of these parameters will be discussed in more detail below. It is the fixing of the two parameters, m and r, that provides the general practical utility of the preferred embodiment of approximate entropy.

Having set these parameters, the present invention proceeds to perform the necessary calculations to compute the approximate entropy measure. The processing means 16 begins by following the steps illustrated in FIG. 5. The numerical data are given as U(1), U(2), . . . , U(nsum). The steps performed by the processing means 16 are performed primarily within a loop where the index of the loop, i, goes from one to the number of elements in the set of data (denoted as nsum) as indicated by steps 30, 32 and 34. At the beginning of this loop, the first locations in two memory arrays are set at a value of zero (the two memory arrays ID(i) and IC(i)). Nested within the larger loop is a smaller loop that has a loop index, j, that also goes from 1 to nsum (steps 30, 36 and 38).

The main part of this algorithm involves calculations to appropriately fill the arrays ID(i) and IC(i), for i=1, 2, . . . , nsum. The final calculation of the approximate entropy follows in a straightforward manner from all these ID and IC values, as discussed below.

Within the inner loop, the variable k is set initially at a value of 1 (step 38). k is used within this inner loop as a counter to keep track of the locations of comparisons. Next, the value of the variable diff is calculated as the absolute value of the difference U(i+k-1) U(j+k-1) (step 40). diff is equal to the absolute value of the difference between the elements within the sets of data that are currently being compared. Once diff is calculated, the system checks to see whether diff is greater than r (step 42). The system, in other words, checks to see whether U(i+k-1) lies within a distance less than the radius (filter) from U(j+k-1). If the diff exceeds the radius, j is incremented (step 38). However, if the difference is less than or equal to the radius, k is incremented (step 44). In the event that k is incremented, the system checks to see whether k is greater than m (step 46). This comparison is to check whether the value being examined lies within or outside the run length currently being compared as designated by m. If k is not greater than m, then diff is recalculated using the new value of k (i.e. step 40 is repeated with the new k). The new value of k shifts the comparison over by one element. For instance, if U(1) and U(2) had been initially compared, after k was incremented the diff value is recalculated between U(2) and U(3).

Suppose, in contrast, that k is greater than m (step 46). In that case, the array location at IC(i) is incremented by 1 (step 48). Furthermore, diff is recalculated to equal the absolute value of U(i+m) U(j+m) (step 50). This calculation is to determine whether the corresponding elements located a run length away from the elements that were just compared are also close enough for their difference to lie within the radius. Step 52 checks to see whether this difference lies within the radius. If the difference is not greater than the radius, the array location ID(i) is incremented by 1 (step 54). If the difference is greater than the radius, the value of j is merely incremented by 1. The steps are repeated until both i and j equal nsum.

For illustrative purposes, suppose that the system processes the data shown in FIG. 4a. Further suppose that m=2 and r=0.5. In the first iteration of the steps shown in FIG. 5, i=1 and j=1. Hence, the difference is calculated as the difference between U(1) and U(1) (step 40). This difference is zero which means that the difference is less than the radius 0.5 (as checked by step 42). As such, k is incremented by 1 (step 44). k, however, is not greater than m (i.e. 2) (step 46); thus, the diff value is recalculated (step 40). This subsequently evaluated diff value is derived by comparing U(2) and U(2). In making that comparison, diff is again 0 (step 42). After incrementing k (step 44), k is greater than m (step 46), so IC(1) is incremented (step 48) from 0 to 1. Then diff is recalculated (step 50) between U(3) and U(3), and since diff=U3)−U(3)=0, ID(1) is incremented by 1, from 0 to 1. (step 54).

Once ID(1) has been incremented, the value of j is also incremented (step 38) to j=2. The result is that diff is next calculated between U(1) and U(2) (step 40). Since the absolute value of diff is greater than the radius (1 is greater than 0.5), the value of j is incremented once again.

With j having a value of 3 and i having a value of 1, the system sets the value k at 1 (step 38), and it then computes the absolute value of the difference between U(1) and U(3) (step 42). Since both U(1) and U(3) are equal to 1, the difference between them equals zero. The difference lies within the radius (see step 42), and k is incremented to have a value of 2 (step 44). The system then compares k with m and determines that k is not greater than m. It subsequently recalculates the diff value using the incremented value of k (i.e. 2). The system compares U(2) with U(4) to produce a diff value (step 40). This diff value is checked in step 42 and equals zero and accordingly, is not greater than r. k is then incremented again (step 44), but this time, k is greater than m. With k being greater than m (as checked in step 46), step 48 is performed which increments the value at IC(1) from 1 to 2. Diff is recalculated for the corresponding values a subpattern length away from the most recently compared values (step 50). In the current case, U(3) is compared with U(5). This difference is not greater than r (see step 52); so, the value at ID(1) is incremented from 1 to 2.

Once ID(1) has been incremented, the value of j is also incremented (step 38). The result is that diff is calculated between U(1) and U(4) (step 40). Since the absolute value of the difference is greater than the radius, the value of j is incremented once again. With j having a value of 5, the comparison between U(1) and U(5) computes a diff value, equal to zero (step 46), that is within the radius (step 42). The values at U(2) and U(6) are next compared. Since the absolute value of the difference (equal to zero) is less than than or equal to the radius (step 42) and k is greater than m (see step 46) after being incremented, the value at IC(1) is incremented from 2 to 3 (step 48). Furthermore, diff is calculated, but it is calculated between U(3) and U(7) (step 50). This absolute value of the difference is less than the radius (i.e. equal to zero as checked in step 52). As a result, the system increments the value at ID(1) from 2 to 3 (step 54). This entire process is repeated until j equals 10 which is the nsum value for the current example. At this point, the ID(1) and IC(1) computation is concluded; both ID(1) and IC(1)=5. The process is then repeated with i set at 2 as opposed to 1, and it is further repeated for the remaining values of i up to nsum. For this example, at the end of the computation, each element of the ID and IC arrays has the value 5.

The above described process basically compares subsets or subpatterns of the data. It first chooses a value at U(i) and finds a U(j) for which the difference between U(i) and U(j) is within the radius, r. Since, in the example, the radius is 0.5 and the example has only integer values, U(i) and U(j) must be identical to lie within the stated radius. Hence, by comparing U(i) with U(j), the system checks for those values in the data that are identical to U(i).

Once an identical value is found, the system checks the next values in the respective subpatterns of data of the values that were just compared to see if they are also identical. When i equals 1 the first subpattern of data is comprised of U(1) and U(2). In the example case, U(1) and U(2) are not identical so U(1) is compared with U(3). This comparison reveals that they are identical. The system as described above then compares the next value in the respective subpatterns: U(2) and U(4). In the above described example these two are identical; hence, the matrix location IC(1) is incremented. IC(1) keeps track of the number of subpatterns identical to the subpatterns that start at U(1). The system, however, performs an additional type of comparison. It also wants to see if the next value that succeeds the subpattern containing U(i) is identical to the next value that succeeds the subpattern containing U(j). If those values are identical, the counter memory location ID(i) is incremented. ID can, thus, fairly be said to check for an additional level of patternness in the data.

When both of the loops have been completed the arrays IC and ID are completely full. Each location contains the number of matches for each respective i value. The system utilizes these arrays to calculate a ratio which is determined for each i. The ratio equals the ID(i) value divided by the IC(i) value. The logarithm of the ratio is then taken for each i, and the resulting logarithms are summed. This sum is divided by the number of data values (i.e. nsum). The resulting value is equal to the average of the logarithms of the ratios. To produce a positive result, the average is multiplied by $-1$ to produce the approximate entropy measure.

The entropy calculation determines the appropriately averaged relationship between the ID(i)'s and the IC(i)'s for all i. Heuristically, approximate entropy measures the (logarithmic) likelihood that runs of patterns that are close remain close on next incremental comparisons. The IC(i)'s measures the regularity (or frequency) of similar patterns; the ID(i)'s measure the stability of these patterns upon incrementing.

The calculation of the approximate entropy measure in the example case of FIG. 5a produces a value of zero. The data in FIG. 5a are completely patterned so the ratio of IC to ID equals 1, for every i, and the log of one equal zero. Thus, the approximate entropy measure equals the sum of a number of zeroes, or zero. In this example, the approximate entropy measure appropriately validates the intuitive conclusion: the completely patterned data produces an approximate entropy value of zero. In contrast, if the data is completely random, and given by white noise, the approximate entropy approaches infinity (as nsum approaches infinity).

FIG. 4b shows an "intermediate" example set of data. In this data set, every third slot is preset, with alternating values of 1 and 0 (U(3)=1, U(6)=0, U(9)=1, U(12)=0, ...). All other slots have either 0 or 1 in them such that the value a slot has is randomly chosen, probability ½ of either 0 or 1. A computation can be performed to that similar to the one performed above for example 4a. For set parameter values of $m \geq 3$ and $r<1$, the approximate entropy of the sequence is computed to equal $(\frac{2}{3})\ln 2$. This result is again consistent with intuition, in the following sense. The approximate entropy $(\frac{2}{3})\ln 2$ is greater than 0, and the sequence in FIG. 4b appears more random, and less patterned than the sequence in FIG. 4a (which yielded the approximate entropy value of 0). In contrast, the sequence in FIG. 4b has a certain measure of patternness, given by the alternating 0's and 1's in every third location. One would expect the sequence to have lower approximate entropy than the sequence consisting entirely of random 0's and 1's in all slots. Indeed, this lastly defined sequence has approximate entropy equal to $\ln 2$, larger than $(\frac{2}{3}) \ln 2$, again confirming intuition. The consistency of the approximate entropy formula with intuition is another important property of this new measure for practical utility.

The above analysis can readily be expressed in mathematical terms. To express the method in such terms, let the input data be a time series denoted as U(i) where i is an index of time that goes from 1 to N. From the U(i), sequences of vectors X(i) are defined by setting $X(i)=[U(i), \ldots, U(i+m-1)]$ where m equals run or subpattern length. In the example illustrated in FIG. 5a, X(1) equals [U(1), U(2)], X(2) equals [U(2), U(3)], etc. X(i) can be thought as the previously discussed runs used in the comparisons. Let $C_i^m(r)$ equal the number of X(j) such that the difference between X(i) and X(j) is less than or equal to the radius r, divided by the number of elements in the data, N. The difference between the vectors X(i) and X(j) is defined as the maximum of the differences of their respective scalar components. $C_i^m(r)$, thus, counts the number of runs that match (i.e. fall within the radius) and divides this number of matches by the number of elements. Knowing $C_i^m(r)$, one then defines $\Phi^m(r)$ as $$\Phi^m(r) = (1/N) \sum_{i=1}^{N} \log C_i^m(r).$$

From this equation, it is clear that $\Phi^m(r)$ is equal to an average of the logarithms of the $C_i^m(r)$ for $i=1, \ldots, N$.

The approximate entropy measure is defined as:

$$\text{approximate entropy} = \Phi^m(r) - \Phi^{m+1}(r)$$

where m, r and N are all fixed. From the previously disclosed equations, the approximate entropy measure can be rewritten by substituting equations for the $\Phi$'s such that $$\text{approximate entropy} = (1/N) \left( \sum_{i=1}^{N} \log C_i^m(r) - \log C_i^{m+1}(r) \right).$$

This equation yields a single value measure of approximate entropy. The value is in the range of zero to infinity. If the value is greater than zero, it means that the system is somewhat unpatterned. Further, higher values of the measure imply lesser degrees of patternness. Thus, the present invention allows one to compare sets of data to determine which exhibit a greater degree of patternness.

As mentioned above, it is crucial, in developing a patternness measure, to produce a formula that is both computable in finite time and robust to the contribution of noise. The fixing of m, the run length or length of a template pattern, as a small integer value, insures computation in finite time in the present invention. The robustness is obtained by careful choice of a value of the radius or filter (r). In choosing r one must consider that noise can dramatically affect the resulting computation if r is chosen too small. In K-S entropy, the entropy is calculated as r approaches zero and, as such, noise dominates the computation, adding significantly to the level of entropy that is measured. In the present invention, the radius r is fixed so as to minimize the effects of the noise in the data on the computation.

FIG. 6 illustrates a comparison of the effects of using approximate entropy on different waveforms as opposed to established measures. Suppose that the data sought to be analyzed ideally represents a discrete sampling from a perfect sine wave as shown in FIG. 6a. Suppose, however, that a small amount of noise corrupts the data as in FIG. 6b. The effect of this noise on an established entropy calculation is great. It dramatically alters the result. The mean and standard deviation are hardly affected, nor is the approximate entropy measure significantly affected. Suppose, however, that the data is like the data shown in FIG. 6c with large errors. The mean and standard deviation are greatly affected. Both entropy and approximate entropy are, in contrast, nearly unaffected. Thus, the present invention obtains the best aspects of both types of established measures.

The present invention filters out the noise by choosing a value of r such that the contribution of noise to the entropy calculation is minimized. A balance is sought in choosing r. If r is too small, noise will corrupt the approximate entropy calculation. If r is too large, too much "fine detail" will be lost to the coarseness of the filter. A choice for r that appears to be desirable, and that has performed well in studies such as the neonatal study described earlier, is $0.3\sigma$ where $\sigma$ is a standard deviation of the data.

While the invention has been particularly shown and described with reference to preferred embodiments thereof, it will be understood by those skilled in the art that various changes in form and details may be made without departing from the spirit and scope of the invention as defined in appended claims.

We claim:

1. A method for processing a set of medical data with a data processing system to determine a relative amount of patterness of the set of medical data comprising the steps of:
   converting measurements of a medical parameter into a set of medical data having values representative of the measured medical parameter;
   storing the set of medical data in the memory of a data processing system,
   operating on the stored set of medical data with a processor of the data processing system, comprising the operating steps of:
   a) defining a class of contiguous runs of prescribed length of the set of medical data;
   b) comparing each element of this class to a plurality of elements of this class to determine regularity and stability of similar patterns among the elements of this class, wherein contribution of noise to determination of regularity and stability is minimized;
   c) assigning and the stability of similar patterns among the elements of this class of medical data as determined by said comparing step;
   d) providing an output signal indicative of a relative amount of patterness of the set of medical data based on an aggregate of the assigned quantitative values;
   e) comparing the output signal to a predetermined value of patterness to produce a comparison result; and
   performing a corrective medical procedure dependent on the comparison result.

2. A method as recited in claim 1 wherein the output measure of patterness of the medical data is an approximation of entropy of the medical data.

3. A method as recited in claim 1 wherein the contribution of noise to the output signal is minimized because the comparing step includes a noise filter.

4. A method as recited in claim 1 further comprising the step of converting the medical data into digital form before performing the comparing step.

5. A method as recited in claim 1 wherein the medical data is electrocardiograph (EKG) data.

6. A method as recited in claim 1 wherein the medical data is electroencephalograph (EEG) data.

7. A method as recited in claim 1 wherein the medical data is endocrine hormone secretion data.

8. A method as recited in claim 1 wherein the medical data is electro-oculogram (EOG) data.

9. A method as recited in claim 1 wherein the medical data is electromyogram (EMG) data.

10. A method as recited in claim 1 wherein the medical data is respiratory measurements.

11. A method for processing electrocardiograph (EKG) data with a data processing system to measure a relative amount of patterness in the set of electrocardiograph (EKG) beat-to-beat heart rate data, comprising the steps of:

converting an analog EKG signal into digital EKG data having values representative of the analog EKG signal;

storing the EKG data in the memory of a data processing system, operating on the stored EKG data with a processor of the data processing system, comprising the operating steps of:
a) extracting R-R intervals from the EKG data;
b) averaging R-R intervals for a length of time to produce a set of R-R interval averages;
c) defining a class of contiguous runs of prescribed length of the set of R-R interval averages;
d) comparing each element of this class to a plurality of the elements of this class to determine regularity and stability of similar patterns among the elements of this class, wherein contribution of noise to determination of regularity and stability is minimized;
e) assigning quantitative values to measure the regularity and the stability of similar patterns among the elements of this class as determined by the comparing step;
f) computing a single measure of the relative amount of patterness in the EKG data based on an aggregate of the assigned quantitative values;
g) comparing the single measure of the relative amount of patterness in the EKG data to a predetermined value of patterness to produce a comparison result; and performing a corrective medical procedure dependent on the comparison result.

12. A method as recited in claim 11 wherein the single measure of patterness is an approximation of entropy.

13. A method as recited in claim 11 wherein the contribution of noise to the single measure is minimized because the comparing step includes a noise filter.

14. A method for processing a set of hormone secretion level data with a data processing system to measure the relative amount of patterness in the set of hormone secretion level data, comprising the steps of:

converting measurements of the level of hormone secretion over a period of time into a set of hormone secretion level data having values representative of the measurements of hormone secretion;

storing the set of hormone secretion level data in the memory of a data processing system, and operating on the stored set of hormone secretion level data with a processor of the data processing system, comprising the operating steps of:
a) defining a class of continuous runs of prescribed length of the hormone secretion level data;
b) comparing each element of this class to a plurality of the elements of this class to determine regularity and stability of similar patterns among the elements of this class, wherein contribution of noise to determination of regularity and stability is minimized;
c) assigning quantitative values to measure the regularity and the stability of similar patterns among the elements of this class as determined by the comparing step;
d) computing a single measure of the relative amount of patterness of the hormone secretion data based on an aggregate of the assigned quantitative values;
e) comparing the single measure of the relative amount of patterness in the hormone secretion data to a predetermined value of patterness to produce a comparison result; and performing a corrective medical procedure dependent on the comparison result.

15. A method as recited in claim 14 wherein the single measure of patterness is an approximation of entropy.

16. A method as recited in claim 14 wherein the contribution of noise to the measurement of regularity and stability is minimized because the comparing step includes a noise filter.

17. A medical monitor for monitoring heart activity of a patient, comprising:
a) an electrocardiograph for monitoring the heart activity of the patient and producing a corresponding set of signals of said heart activity;
b) a processor for receiving the set of signals of heart activity and processing the signals wherein said processor comprises:
1) means for defining a class of contiguous runs of prescribed length of the set of signals of heart activity;
2) comparision means for comparing each element of this class to a plurality of the elements of this class to determine regularity and stability of similar patterns among the elements of this class, wherein contributions of noise to determination of regularity and stability is minimized;
3) assignment means for assigning quantitative values to measure the regularity and the stability of similar patterns among the elements of this class of the set of signals of heart activity as determined by the comparing of the elements of this class; and
4) output means for providing an output signal indicative of a relative amount of patterness of the set of signals of heart activity based on an aggregate of the assigned quantitative values; and
c) an output device for receiving and responding to the output signal and for providing a corrective medical procedure dependent on the output signal.

18. A medical monitor as recited in claim 17 wherein the output device includes an alarm which sounds when the output signal indicates a low degree of patterness in the set of signals of heart activity.

19. A medical monitor as recited in claim 17 wherein the output device includes a meter that displays an amount of patterness that is indicated by the output signal in the set of signals of heart activity.

20. A medical monitor as recited in claim 17 wherein the output device includes a recording means for recording an amount of patterness that is indicated by the output signal in the set of signals of heart activity.

21. A medical monitor as recited in claim 17 wherein the output device includes an automated corrective medical procedure means that executes a corrective. medical procedure if the output signal indicates a degree of patterness in the set of signals of heart activity.

22. A data processing system for operating on a sequence of data comprising:

storage means for storing the sequence of data in the memory of a data processing system, processing means for operating on the stored sequence of data, the processing means comprising:
a) an assigning means for defining a class of contiguous runs of prescribed length of the sequence of data;
b) a comparing means for comparing each element of this class to a plurality of the elements of this class to determine regularity and stability of similar patterns among the element of this class wherein said comparing means assigns quantitative values to an extent of regularity and stability of similar patterns among elements of this class;
c) a filtering means for minimizing effects of noise from the sequence of data from the values that are compared; and
d) a computational means for using said quantitative values produced by said comparing means to compute a single output approximation of entropy; and automated dispensing means for automatically dispensing medication in response to the approximation of entropy.

* * * * *

UNITED STATES PATENT AND TRADEMARK OFFICE
CERTIFICATE OF CORRECTION

PATENT NO. : 5,191,524                    Page 1 of 2

DATED      : March 2, 1993

INVENTOR(S) : Steven M. Pincus et al.

Figure 5:
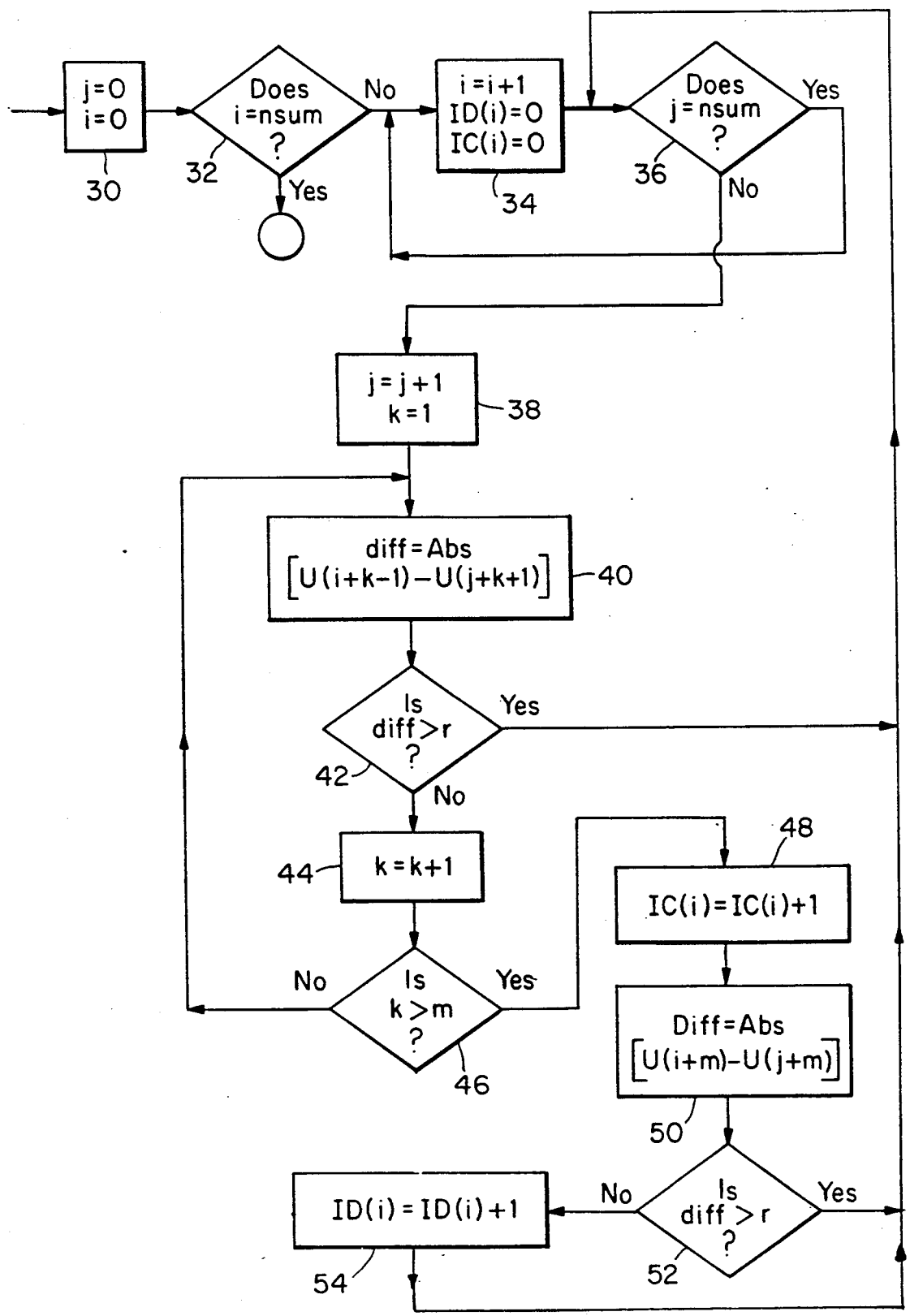
FIG. 5 shows a flow chart of how the approximate entropy measure is calculated.

It is certified that error appears in the above-identified patent and that said Letters Patent is hereby corrected as shown below:

Drawings:
In Figure 5, box 40, change "U(j+k+1) to ---U(j+k-1)---.

In Claim 1, column 12, line 17, change "patterness" to
   ---patternness---; line 23, change "," to ---;---;
   line 30, change "of elements" to ---of the elements---;
   line 35, change "assigning" to ---assigning quantitative
   values to measure the regularity---; and lines 39 and 43,
   change "patterness" to ---patternness---.

In Claim 2, column 12, line 48, change "patterness" to
   ---patternness---.

In Claim 11, column 13, lines 3, 30, 33 and 34, change
   "patterness" to ---patternness---.

In Claim 12, column 13, line 39, change "patterness" to
   ---patternness---.

In Claim 14, column 13, line 45 and column 14, lines 2, 6
   and 7, change "patterness" to ---patternness---.

In Claim 15, column 14, line 12, change "patterness" to
   ---patternness---.

In Claim 17, column 14, line 41, change "patterness" to
   ---patternness---.

In Claim 18, column 14, line 50, change "patterness" to
   ---patternness---.

In Claim 19, column 14, line 54, change "patterness" to
   ---patternness---.

UNITED STATES PATENT AND TRADEMARK OFFICE
CERTIFICATE OF CORRECTION

PATENT NO. : 5,191,524
DATED : March 2, 1993
INVENTOR(S) : Steven M. Pincus et al.

It is certified that error appears in the above-identified patent and that said Letters Patent is hereby corrected as shown below:

In Claim 20, column 14, line 58, change "patterness" to ---patternness---.

In Claim 21, column 14, line 64, change "patterness" to ---patternness---.

In Claim 22, column 14, line 68, change "," to ---;---.

Signed and Sealed this

Fourth Day of June, 1996

Attest:

BRUCE LEHMAN

Attesting Officer     Commissioner of Patents and Trademarks